United States Patent [19]

Lask et al.

[11] Patent Number: 4,924,084
[45] Date of Patent: May 8, 1990

[54] DEVICE FOR DETERMINING SURFACE MOISTURE

[75] Inventors: Helmut Lask, Eltville; Arno Holst, Wiesbaden; Kurt Dryczynski, deceased, late of Hofheim am Taunus, Fed. Rep. of Germany, by Christa Magdalene Dryczynski, Thomas Dryczynski, Beate Dryczynski, Regina Struth née Dryczynski, legal heirs

[73] Assignee: Hoechst Aktiengesellschaft, Fed. Rep. of Germany

[21] Appl. No.: 257,327

[22] Filed: Oct. 13, 1988

[30] Foreign Application Priority Data

Oct. 17, 1987 [DE] Fed. Rep. of Germany ....... 3735269

[51] Int. Cl.$^5$ ............................................. G01N 21/49
[52] U.S. Cl. .............................. 250/227.25; 250/577; 250/903
[58] Field of Search ...................... 250/577, 227, 216; 73/293; 340/619; 356/135, 136

[56] References Cited

U.S. PATENT DOCUMENTS

| 3,120,125 | 2/1964 | Vasel | 73/293 |
|---|---|---|---|
| 3,487,069 | 12/1969 | Maselli | 356/135 |
| 3,882,887 | 5/1975 | Rekai | 250/577 |
| 4,699,516 | 10/1987 | Bartz et al. | 356/136 |
| 4,788,444 | 11/1988 | Williams | 250/577 |

FOREIGN PATENT DOCUMENTS 1151301 5/1969 United Kingdom ................ 356/135

Primary Examiner—Edward P. Westin
Attorney, Agent, or Firm—Connolly & Hutz

[57] ABSTRACT

A device for determining surface moisture, especially of absorbent materials, comprises a Dove reflection prism, a radiation source of such a design that its beams, which are aligned parallel, perpendicularly strike one of the two small surfaces of the prism, a light trap which traps the light beams emanating from the other small surface, and a photoelectric transducer which is located in the angle formed by the two small surfaces and is arranged such that its measurement surface is located parallel and opposite to the hypotenuse surface of the prism.

2 Claims, 5 Drawing Sheets

DEVICE FOR DETERMINING SURFACE MOISTURE

BACKGROUND OF THE INVENTION

The invention relates to a device which is suitable for determining the surface moisture of, in particular, absorbent, fluid-absorbing or fluid-transporting two-dimensional structures such as, for example, filter paper, baby diapers, sanitary towels, incontinence diapers, patient underlays, nonwovens or textiles. In addition, in the case of materials of homogeneous moisture distribution, the surface measurement can provide information on the moisture content in the interior of a system.

For the assessment of materials of the type described above, it is frequently necessary to know the moisture conditions on the surface or in the interior of the system, above all when their use value is mainly determined by this parameter. This is the case, for example, with baby diapers, incontinence diapers, patient underlays and textiles which come into direct contact with the skin. In many cases, the moisture conditions at the surface are correlated with those in the overall system. However, this is not always the case, in particular if the structures to be examined are composed of several layers of different suction capacity and absorbency. Hygiene articles, medical underlays and towels may be mentioned as examples thereof. These are composed of a highly absorbent core and a covering layer of greatly reduced fluid absorption, such as, for example a polypropylene nonwoven.

A large number of methods and devices for the measurement of moisture are known. Thus, these can be determined on the object, for example via changes in conductivity, inductivity, capacitance or the intensity of IR radiation. Frequently, however, these methods have the feature that they cover not only the surface conditions of the system but also deeper layers. By contrast, using the measuring apparatus described in accordance with the invention, it is possible to determine the moisture conditions on the surface and hence to detect the surface moisture, for example in the case of contact with the skin, in a manner which is substantially closer to practice than in other methods.

SUMMARY OF THE INVENTION

The invention relates to a device for determining surface moisture, which comprises a Dove reflection prism, a radiation source of such a design that its beams perpendicularly strike one of the two small surfaces, a light trap which traps the light beams emanating from the other small surface, and a photoelectric transducer which is located in the angle formed by the two small surfaces and is arranged such that its measurement surface is located parallel and opposite to the hypotenuse of the reflection prism.

DETAILED DESCRIPTION OF THE INVENTION

Figure 1:
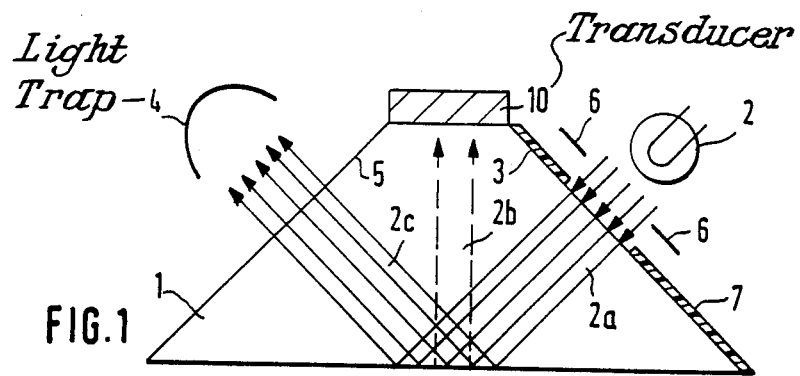
FIG. 1 is a diagrammatic sectional view of a device for determining surface moisture, according to the present invention.

A preferred embodiment of this type is shown in FIG. 1. In the case of a rectangular prism (1), a light source (2) is fitted above one of the small surfaces (3). The parallel light beams originating from this light source pass through the prism and strike the glass/air interface at the hypotenuse surface. For parallel alignment of the light beams, diaphragms (6) can be provided in the optical path, and the small surface can be covered by an opaque layer (7) in the areas where there is to be no incidence of light. If the hypotenuse surface of this prism then rests on a dry surface, there is total reflection of the incident light, because of the slight contact between the glass and the surface of the object which is to be measured, and the predominant part leaves the prism through the second small surface (5) and is absorbed by the light trap (4). Corresponding to the small contact areas, a small proportion of scattered light (2b) is generated which reaches the photoelectric transducer (10). The light trap is in the form of a black cavity. In the case of a design of this device in a manner appropriate to practice, the housing can be used as such a light trap, if it is roughened and blackened.

Figure 2:
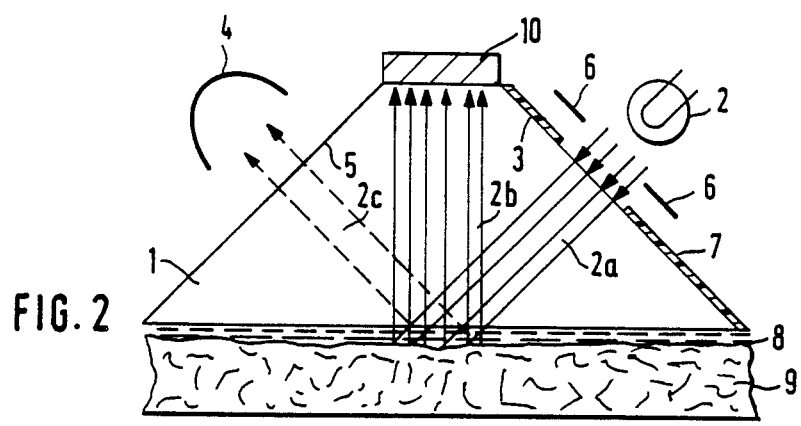
FIG. 2 is a view similar to FIG. 1 with the device resting on a moist surface.

If the hypotenuse surface of the prism rests on a moist surface, as shown in FIG. 2, the light beam leaves the prism at the hypotenuse surface and is scattered at the irregular surface (8) of the test specimen (9). The predominant part of the scattered light (2a) passes back into the glass prism and strikes a photoelectric transducer (10) which is located in the angle of the two small surfaces precisely opposite the hypotenuse surface. The voltage generated in this photoelectric transducer is proportional to the moisture layer on the surface of the test specimen and is indicated by appropriate measuring instruments. By means of a recorder, the measurement steps can be advantageously recorded as a function of time.

For a perfect measurement, the hypotenuse surface of the prism must remain in direct contact with the surface to be tested. This is achieved already by the own weight of the prism resting on the surface which is to be tested. By placing additional weights on top, this contact with the surface which is to be measured, especially in the case of soft elastic objects such as, for instance, diapers, can be intensified. Conversely, it is also possible to minimize the bearing weight by turning the prism over in such a way that the hypotenuse surface lies at the top and the object which is to be measured is then placed upon the hypotenuse surface. With such a type of measurement, however, incidence of extraneous light must be prevented.

The device according to the invention can be used for quantitative measurements, but must then be calibrated beforehand. This is done by means of absorbent materials, the moisture content of which is the same throughout the volume. This state is obtained by impregnating the absorbent body with fluid up to the maximum and adjusting it to the preset moisture value by centrifuging. In this way, a calibration curve is obtained which is characteristic of the absorbent body to be examined, of the lamp brightness applied and of the given loading of the measuring head. Additional use of a linear amplifier has the result that the photocell used operates with short-circuit current. This gives a linear relationship between the measured light intensity and the voltage output. The otherwise slightly curved calibration lines become straight lines.

Figure 3:
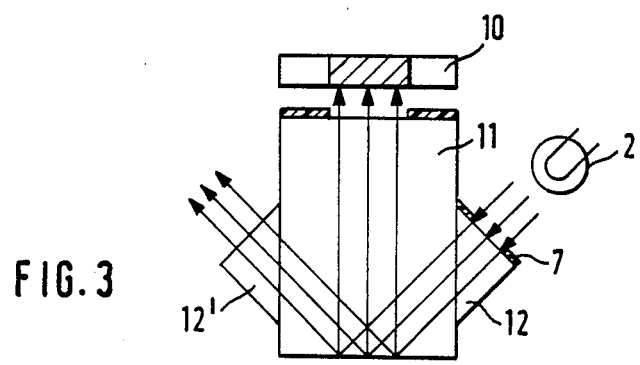
FIG. 3 is a diagrammatic sectional view of an alternate embodiment of the device shown in FIGS. 1 and 2.

Another embodiment of the device according to the invention is shown in FIG. 3. In place of the rectangular prism, a cuboid block (11) is used here. One prism (12 and 12') is fitted to each of two opposite sides of this block, in particular in such a way that the block together with the two prisms allows the same optical path as in the prism according to FIG. 1. The photoelectric transducer is here located on the upper boundary face of the cuboid.

EXAMPLE 1

The example shows the calibration of the system, taking the example of a highly absorbent filter paper (weight per unit area: 150 g/m$^2$). By impregnation with water and subsequent suction with another filter paper or by centrifuging off, papers of different water content were prepared. With the aid of a linear amplifier, the scale divisions, corresponding to the moisture content, of a line recorder connected thereto were determined under a load of 30 g/cm$^2$.

Figure 4:
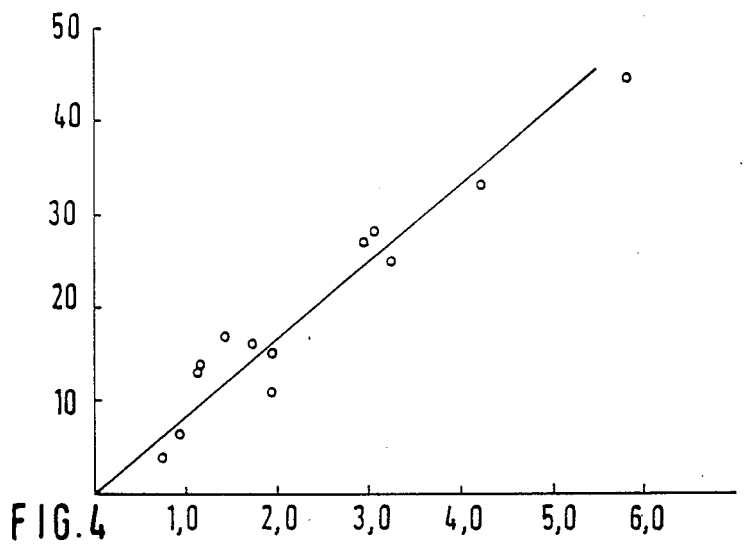
FIG. 4 is a plot of Example 1 illustrating calibration of the device.

| Moisture content g of H$_2$O/g of paper | Recorder indication scale divisions |
| --- | --- |
| 0 | 0 |
| 0.5 | 4 |
| 0.7 | 4 |
| 0.9 | 6 |
| 1.1 | 13 |
| 1.1 | 14 |
| 1.1 | 9 |
| 1.2 | 10 |
| 1.4 | 17 |
| 1.7 | 14 |
| 1.7 | 16 |
| 1.9 | 15 |
| 1.9 | 11 |
| 2.3 | 19 |
| 2.9 | 27 |
| 3.0 | 28 |
| 3.2 | 25 |
| 4.2 | 33 |
| 5.8 | 44 |
| maximum absorption (see also FIG. 4) | 64   r = 0.9710 |

EXAMPLE 2

The example shows the effect of the moisture content of a baby diaper on the surface moisture with and without a covering nonwoven. As the test object, a segment of 10×12.5 cm in size from a diaper of the PAMPERS maxi plus type was impregnated homogeneously with water and adjusted to various moisture contents as in Example 1.

| Moisture content g of H$_2$O/ g of diaper | Diaper without nonwoven | Moisture content g of H$_2$O/ g of diaper | Diaper with nonwoven |
| --- | --- | --- | --- |
| 0 | 0 | 0.5 | 2 |
| 1.7 | 14 | 1.0 | 2 |
| 2.1 | 16 | 1.5 | 2 |
| 2.2 | 27 | 2.1 | 2 |
| 2.6 | 23 | 2.7 | 2 |
| 2.6 | 24 | 3.1 | 2 |
| 2.7 | 28 | 3.5 | 2 |
| 3.2 | 27 | 4.2 | 2 |

-continued

| Moisture content g of H$_2$O/ g of diaper | Diaper without nonwoven | Moisture content g of H$_2$O/ g of diaper | Diaper with nonwoven |
| --- | --- | --- | --- |
| 3.5 | 30 | 4.5 | 19 |
| 3.8 | 31 | 4.7 | 21 |
| 3.9 | 38 | 5.2 | 51 |
| 4.8 | 42 | 5.7 | 60 |
| 5.4 | 42 | max. absorption | 61 |
| 5.7 | 48 | 5.9 | 54 |
| 6.1 | 51 | 6.0 | 59 |
| max. absorption   r = 0.9757 | | r$_{(4.2-6.0)}$ = 0.9554 | |

Figure 5:
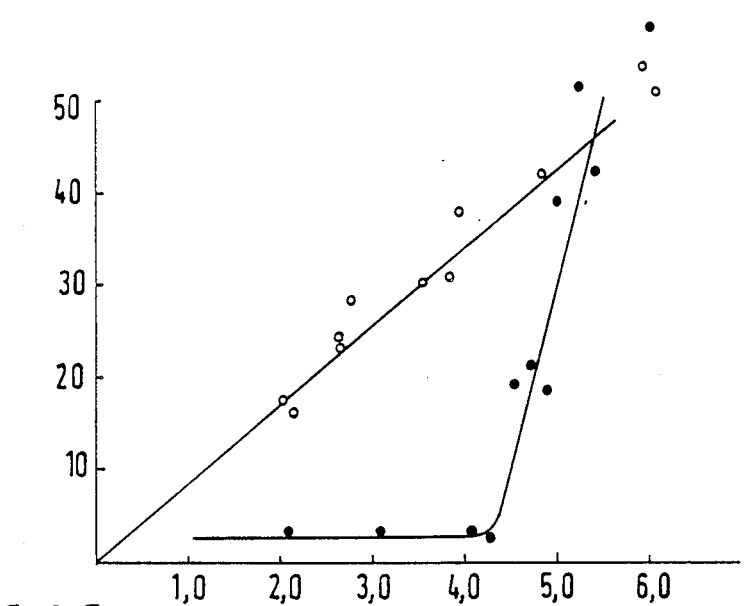
FIG. 5 is a plot of Example 2.

The results are shown graphically in FIG. 5.

Referring to these results, it will be seen that a dry surface is obtained by the use of a polypropylene covering nonwoven, even through the actual absorbent material has already reached a highly moist state with about 70% of the maximum quantity of fluid. These states are also evaluated correspondingly by means of tactile assessment. It is thus possible numerically to allocate the tactile examination required for evaluating the suitability for use, and to determine it. Moreover, by means of the method and device described, it is possible numerically to establish the quantity of fluid which may still be present in free mobility in an absorbent pad such as, for example, a baby diaper, apart from the absorptively bound fluid, without the skin being moistened.

In an examination of "wetback", hitherto customary in the field of hygiene, filter paper is placed upon the absorbent body, and the quantity of fluid which can be sucked out under load is determined. This method only incompletely simulates the conditions at the boundary face between the covering nonwoven of the diaper and the baby's skin. In the case of a diaper, the measurements by the method and device according to the invention show the transition from dry to wet in a manner which is much closer to practice than the wetback test. Thus, this invention can advantageously be utilized in the development of hygiene articles and medical underlays. If the conditions in the absorbent pad are kept constant, it is also possible to carry out an evaluation of covering nonwoven materials.

EXAMPLE 3

This example shows how dynamically proceeding events in absorbent systems can be investigated and assessed by means of the invention.

In the development of absorbent bodies such as, for example, baby diapers, it is important to know how the fluid to be absorbed is distributed in the diaper in the course of time. Since there is a mutual influence of all the materials concerned in this case, the surface moisture measurement can also be applied advantageously in this case. Thus, not only the rate of migration of the fluid in the capillary-active system (drainage), but additionally the partial degree of saturation can be determined as the ratio of the existing moisture content to the maximum moisture content. In these measurements, the covering nonwoven must be removed at the measuring point, in order to exclude the influence explained in Example 2.

Figure 6:
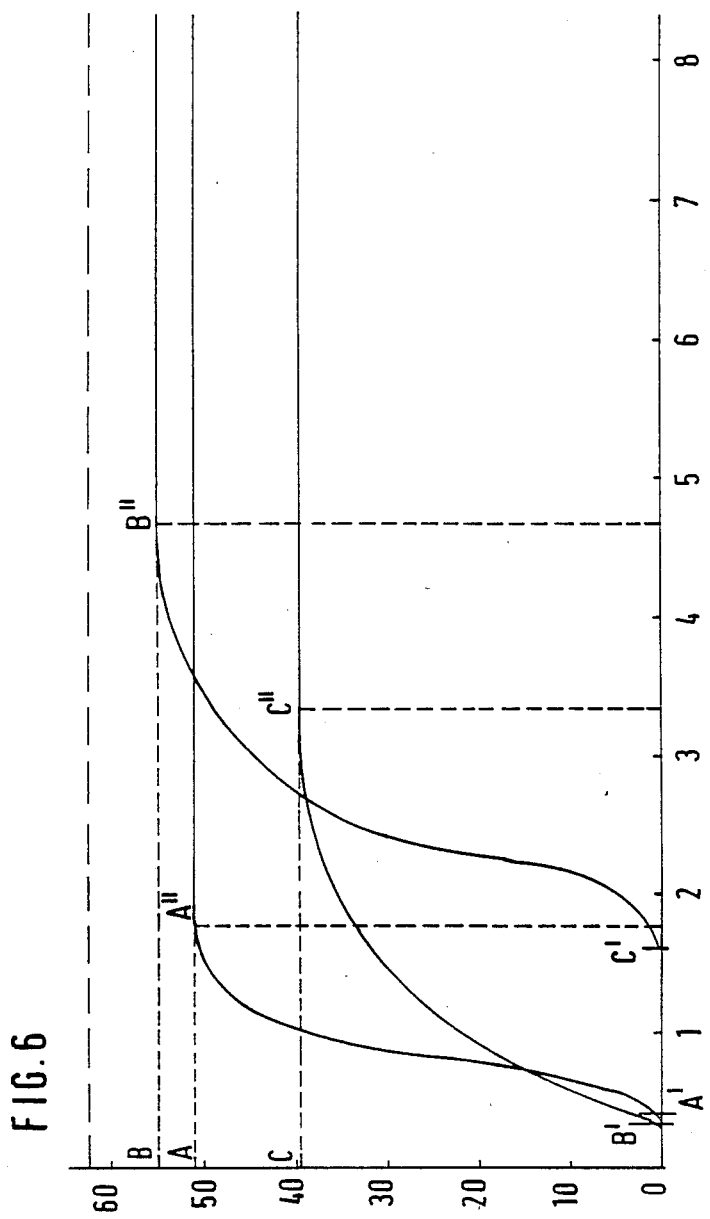
FIG. 6 is a plot of Example 3.

FIG. 6 shows three typical shapes of curves. For each absorbent body 3, they show characteristic measured points (A, B, C=relative final moisture content; A', B', C'=time of the start of moistening; A", B", C"=time of the end of moistening). The distance between the point of application of fluid and the measuring point can here be freely selected.

Very recently, diapers increasingly contain superabsorbent polymers (SAP). By means of these substances, the diaper structure can be completely redesigned and optimized. When a superabsorbent polymer is used, a diaper contains a further component which has a substantial influence on the fluid absorption, absorption rate and retention.

Via the measurement of surface moisture by means of the invention, the influence of placing can also be described, as shown by Example 4.

EXAMPLE 4

Figure 7:
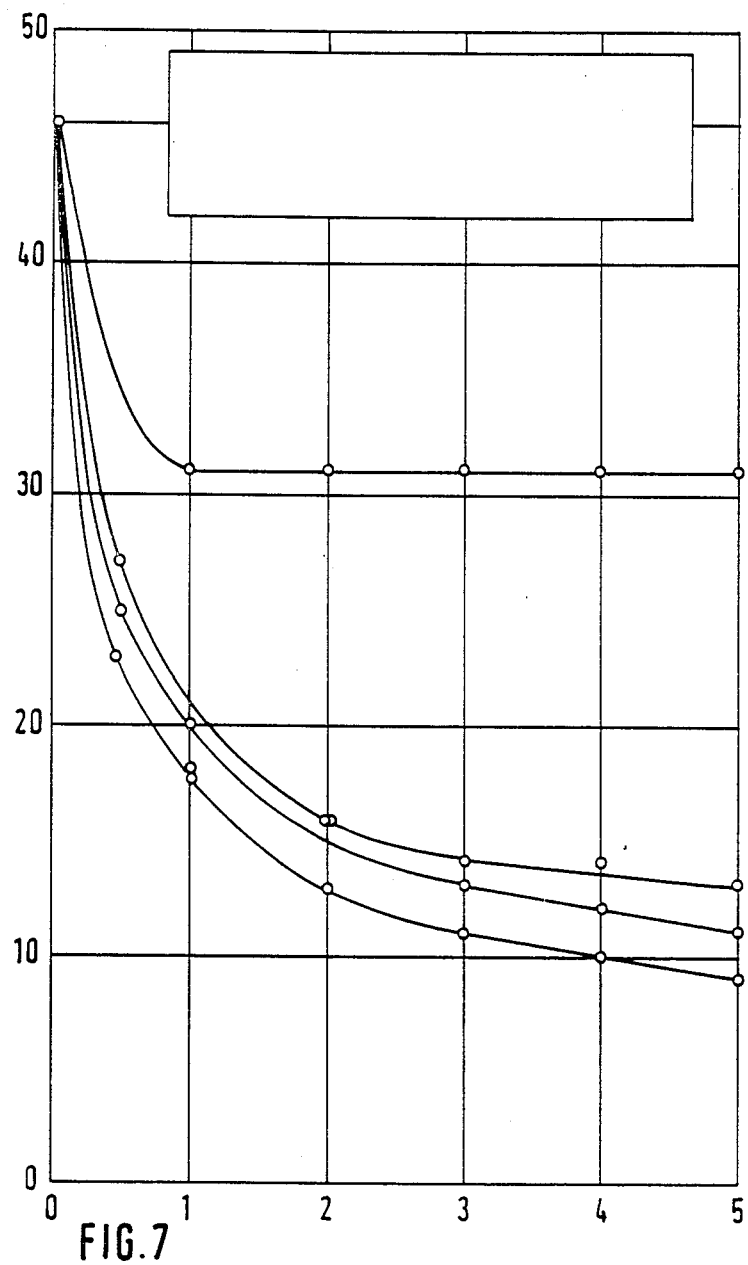
FIG. 7 is a plot of Example 4.

1.0 g of a superabsorbent polymer is added to a Pampers maxi plus diaper segment (10×10 cm) between the fluff and covering nonwoven (top), in the middle ply (middle) and between the fluff and backsheet (bottom), and the decrease in surface moisture with time after addition of 40 ml of 0.9% NaCl solution is determined by comparison with a diaper without SAP. The results are shown in FIG. 7. It can be seen from the diagrams that the diaper surface becomes the drier, the closer the superabsorbent is placed to the surface of the diaper.

The influence of SAP of different provenance on the absorption and retention processes in an absorbent body can also be characterized in the following measuring arrangement.

EXAMPLE 5

Figure 8:
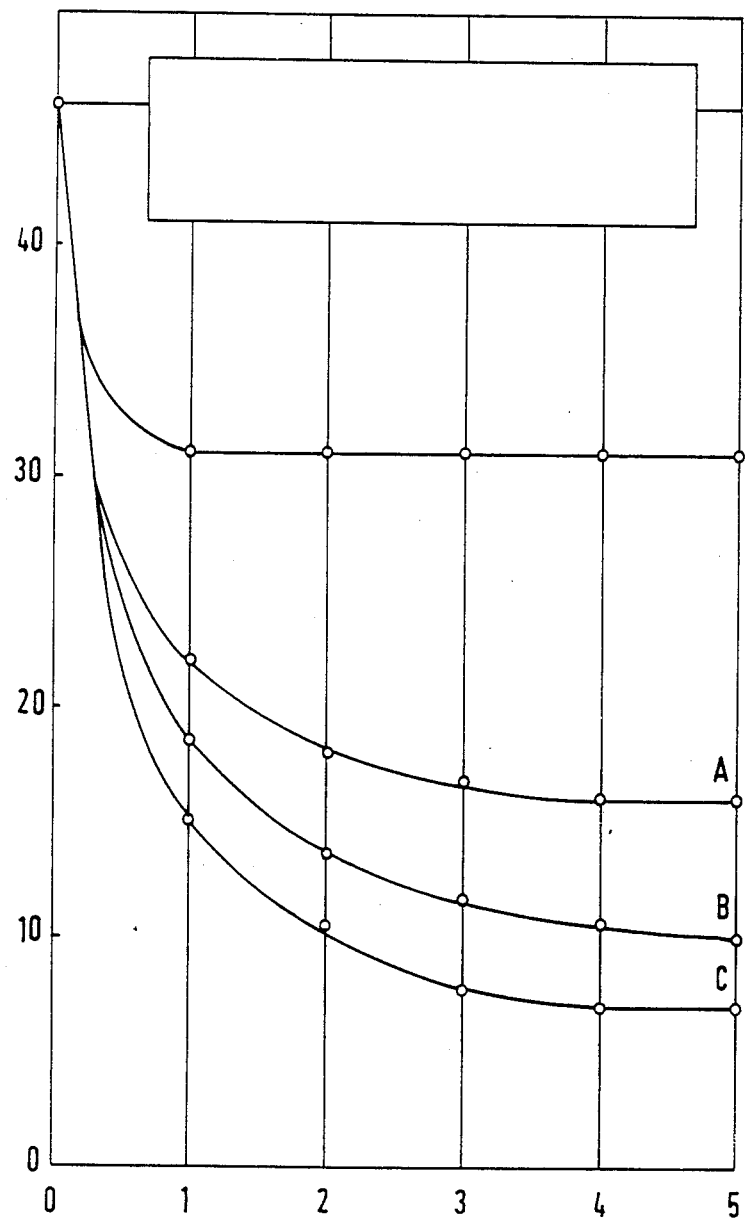
FIG. 8 is a plot of Example 5.

0.5 g of superabsorbent polymer of different provenance, but of comparable absorptive capacity, is homogeneously distributed between the absorbent pad and the covering nonwoven in a 12.5×10 cm Pampers maxi plus diaper with about 14 g of cellulose. 40 ml of 0.9% NaCl are then centrally poured into a metal ring of 6 cm diameter. About 5 seconds after the fluid has penetrated the absorbent body, the metal ring is removed, the measuring head of the device according to the invention is placed upon the moistened diaper and the recorder is started. The measurement is terminated after 5 minutes. It can be seen from the diagram in FIG. 8 that, when SAP is used, redrying of a diaper surface is markedly improved over a comparison diaper without SAP. Furthermore, the three absorbent polymers used show different effects on the surface moisture. The example shows that the invention is also suitable for assessing and characterizing the influence of different superabsorbent polymers on the surface dryness.

The invention can also be used with advantage in the evaluation of the moisture content of textiles, as shown by the following example.

EXAMPLE 6

A desized cotton fabric (weight per unit area 158 g/cm$^2$) is charged with different quantities of moisture and measured in the manner described:

| Moisture content g of H$_2$O/g of fabric | recorder indication scale divisions |
| --- | --- |
| 0.2 | 4 |
| 0.53 | 9 |
| 0.7 | 12 |
| 0.8 | 17 |
| 1.0 | 32 |
| 1.37 | 43 |
| 1.35 | 38 |
|  | r = 0.967 |
| max. | 40 |

We claim:

1. A device for determining surface moisture, which comprises a Dove reflection prism (1), a radiation source (2) of such a design that its beams (2a), which are aligned parallel, perpendicularly strike one of the two small surfaces (3) of the prism, a light trap (4) which traps the light beams (2c) emanating from the other small surface (5), and a photoelectric transducer (10) which is located in the angle formed by the two small surfaces and is arranged such that its measurement surface is located parallel and opposite to the hypotenuse surface of the prism, and which converts the light (2b) scattered by the surface which is to be measured.

2. A device for determining surface moisture, which comprises a cuboid block (11) having two opposite parallel sides, a flat bottom surface and a top surface parallel to the bottom surface, two prisms (12 and 12'), one attached to each of the two opposite sides of the cuboid block, a radiation source (2) of such a design that its beams (2a), which are aligned parallel, perpendicularly strike one of the two prisms, and a photoelectric transducer (10) which is located in the angle formed by the two prisms and is arranged such that its measurement surface is located parallel and opposite to the bottom surface of the cuboid block, and which converts the light (2b) scattered by the surface which is to be measured.

* * * * *